United States Patent
Mirov et al.

(10) Patent No.: US 12,408,868 B1
(45) Date of Patent: Sep. 9, 2025

(54) SYSTEMS AND METHODS FOR PEEL-OFF DETECTION FOR LOW-POWER ELECTRONICS

(71) Applicant: Verily Life Sciences LLC, South San Francisco, CA (US)

(72) Inventors: Russell Mirov, Los Altos, CA (US); Benjamin Krasnow, Redwood City, CA (US); Brett Schleicher, San Francisco, CA (US)

(73) Assignee: Verily Life Sciences LLC, Dallas, TX (US)

( * ) Notice: Subject to any disclaimer, the term of this patent is extended or adjusted under 35 U.S.C. 154(b) by 1164 days.

(21) Appl. No.: 16/791,187

(22) Filed: Feb. 14, 2020

Related U.S. Application Data (60) Provisional application No. 62/806,001, filed on Feb. 15, 2019.

(51) Int. Cl.
*A61B 5/00* (2006.01)
*A61B 5/145* (2006.01)
(Continued)

(52) U.S. Cl.
CPC ........ *A61B 5/68335* (2017.08); *A61B 5/0002* (2013.01); *A61B 5/14532* (2013.01);
(Continued)

(58) Field of Classification Search
CPC .............. A61B 5/68335; A61B 5/0002; A61B 5/14532; A61B 5/1477; A61B 5/6833;
(Continued)

(56) References Cited

U.S. PATENT DOCUMENTS

| | | |
|---|---|---|
| 9,431,354 B2 | 8/2016 | Cabral, Jr. et al. |
| 2002/0049389 A1* | 4/2002 | Abreu ............... G02C 7/04 600/318 |

(Continued)

FOREIGN PATENT DOCUMENTS

KR    101706499    2/2017

OTHER PUBLICATIONS

Induced. 2019. In Merriam-Webster.com. Retrived Feb. 13, 2019, from https://www.merriam-webster.com/dictionary/induce (Year: 2019).*

(Continued)

*Primary Examiner* — Jason M Sims
*Assistant Examiner* — Kyle W. Kretzer
(74) *Attorney, Agent, or Firm* — Kilpatrick Townsend & Stockton LLP (57) ABSTRACT

Systems and methods for peel-off detection for lower power electronics are disclosed. In one embodiment, a device includes: a housing; sensor electronics disposed within the housing; an electrode positioned to receive a charge and output a control signal upon removal of a material positioned proximate to the electrode; an electronic switch configured to control an electrical connection between a power supply and the sensor electronics; and an amplifier electrically coupled to the electrode and configured to receive the control signal from the electrode and output an amplified signal to change a state of the electronic switch based on the control signal.

20 Claims, 6 Drawing Sheets

(51) Int. Cl.
*A61B 5/1477* (2006.01)
*G01D 11/24* (2006.01)

(52) U.S. Cl.
CPC .......... *A61B 5/1477* (2013.01); *A61B 5/6833* (2013.01); *G01D 11/245* (2013.01); *A61B 2560/0209* (2013.01)

(58) Field of Classification Search
CPC .......... A61B 2560/0209; G01D 11/245; G06F 1/3206
USPC .......................................................... 600/347
See application file for complete search history.

(56) References Cited

U.S. PATENT DOCUMENTS

| | | | | |
|---|---|---|---|---|
| 2009/0076336 | A1* | 3/2009 | Mazar | A61B 5/6843 600/300 |
| 2010/0286607 | A1* | 11/2010 | Saltzstein | A61B 5/6848 604/93.01 |
| 2016/0354072 | A1* | 12/2016 | Swift | A61B 90/30 |
| 2018/0263538 | A1* | 9/2018 | Heikenfeld | A61B 5/14521 |
| 2018/0289973 | A1* | 10/2018 | Carney | A61N 1/3962 |
| 2020/0008675 | A1* | 1/2020 | Heikkilä | A61B 5/02438 |
| 2020/0253525 | A1* | 8/2020 | Zhang | H05K 1/11 |

OTHER PUBLICATIONS

Fiveable. "Induced Charge—Principles of Physics II." Edited by Becky Bahr, Fiveable, 2024, https://library.fiveable.me/key-terms/principles-physics-ii/induced-charge. Accessed May 14, 2025. (Year: 2024).*

Wizeprep. "1.1.2 Conductors, Insulators, and Induced Charge", 2025, https://https://www.wizeprep.com/online-courses/20116/chapter/1/core/1/2. Accessed May 14, 2025. (Year: 2025).*

A. Pedersen, G. C. Crichton and I. W. McAllister, "The functional relation between partial discharges and induced charge," in IEEE Transactions on Dielectrics and Electrical Insulation, vol. 2, No. 4, pp. 535-543, Aug. 1995, doi: 10.1109/94.407019. (Year: 1995).*

* cited by examiner

SYSTEMS AND METHODS FOR PEEL-OFF DETECTION FOR LOW-POWER ELECTRONICS

CROSS-REFERENCE TO RELATED APPLICATIONS

This application claims priority to U.S. Provisional Patent Application No. 62/806,001, titled "Systems And Methods For Peel-Off Detection For Low-Power Electronics," filed Feb. 15, 2019, the entirety of which is hereby incorporated by reference.

BACKGROUND

Single use wearable sensors are becoming more popular. For many such sensors the period of time the sensor is worn by the user is a relatively small percentage of the lifetime of the sensor. For example, these sensors may include active components, e.g., a processor, memory, sensor, etc., which are powered by an onboard battery. However, one or more of these components may consume energy when the device is technically "off." For example, in some devices the processor must remain in a "low power" mode to detect whether the user has pressed the "on" button. However, storage and shipment prior to use may take many months. Thus, a significant portion of the total battery capacity may be consumed during storage prior to activation by the end user.

SUMMARY

In one embodiment, a system of the present disclosure may comprise: a device comprising: a housing; sensor electronics disposed within the housing; an electrode positioned to receive a charge and output a control signal upon removal of a material positioned proximate to the electrode; an electronic switch configured to control an electrical connection between a power supply and the sensor electronics; and an amplifier electrically coupled to the electrode and configured to receive the control signal from the electrode and output an amplified signal to change a state of the electronic switch based on the control signal.

Another embodiment of the present disclosure may comprise: an electronic device comprising: an electrode configured to output a control signal upon removal of a material; an electronic switch configured to control an electrical connection between a power supply and one or more active components; and an amplifier configured to receive the control signal from the electrode and output a signal to change a state of the electronic switch based on the control signal.

In one embodiment, a method of the present disclosure may comprise a method for activating an electronic device comprising: receiving, by an electrode of the electronic device, a charge in response to removal of a material from a housing of the electronic device; amplifying the charge; and closing a switch based on the amplified charge to provide power to one or more active components.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

A full and enabling disclosure is set forth more particularly in the remainder of the specification. The specification makes reference to the following appended figures.

DETAILED DESCRIPTION

Reference will now be made in detail to various and alternative illustrative embodiments and to the accompanying drawings. Each example is provided by way of explanation, and not as a limitation. It will be apparent to those skilled in the art that modifications and variations can be made. For instance, features illustrated or described as part of one embodiment may be used in another embodiment to yield a still further embodiment. Thus, it is intended that this disclosure include modifications and variations as come within the scope of the appended claims and their equivalents.

Illustrative Example of Peel-Off Detection for Low-Power Electronics

One illustrative embodiment of the present disclosure includes a single use analyte sensor. For example, one such device may include a single use glucose sensing patch. Such a patch may be worn by the user for a predetermined time to measure the user's glucose levels during that time and then discarded and replaced by a new patch. The illustrative glucose sensing patch includes active components, e.g., a processor, memory, sensor, etc., which are powered by an onboard battery as well as circuitry to prevent these active components from consuming energy until the device is in use. Thus, the illustrative glucose sensing patch can be stored for a longer period of time and/or be manufactured with a smaller or less expensive battery than a conventional patch.

The illustrative glucose sensing patch includes an electrode covered by a passive material (e.g., a mylar tape). When the passive material is removed a separation charge or induced charge generates a voltage across the electrode. This voltage is output to an amplifier circuit, e.g., a single transistor amplifier (e.g., an npn transistor configured as a common emitter amplifier). The amplifier circuit receives the voltage from the electrode, amplifies this voltage, and outputs the amplified voltage to an electronic switch (e.g., a transistor (e.g., a BJT or MOSFET), a relay, an electronically controlled switch, or other switching circuit) to control the flow of current from a power supply (e.g., a battery) to the active components (e.g., processor, memory, sensors, network interfaces, etc.). Alternatively, in some embodiments the output of the amplifier may be used to wake a processor from a deep-sleep state, such as by disabling a RESET line on the processor or activating a clock.

In the illustrative glucose sensing patch, once the switch is closed and the active components are powered, the sensor activates and measures glucose (or some other analyte). The processor records these measurements in a memory. After a period of time the illustrative patch may transmit the stored data to a remote device (e.g., a mobile device) via a network connection (e.g., a Bluetooth, WiFi, or NFC network connection).

In some embodiments the passive material may cover certain components to ensure that the user removes the passive material and thus activates the glucose sensing patch. For example, in some embodiments, the passive material may be positioned to cover parts of components that need to be positioned to activate the glucose sensing patch. In such an embodiment, the passive material may cover sensor components in addition to the electrode (e.g., a sensor probe or wire). In other embodiments, the passive material may cover information, e.g., network connection information, thus providing a requirement that the user remove the passive material. In still other embodiments the passive material may couple the glucose sensing patch to its packaging. Thus, removing the passive material, and thereby activating the glucose sensing patch, is a necessary step in removing the glucose sensing patch from its packaging.

The solution described above enables the illustrative glucose sensing patch to have a longer battery life because active components in the glucose sensing patch (e.g., the processor, memory, etc.) do not draw power from the battery until activated by removing the tape. This may enable a relatively smaller, lighter, and cheaper battery to be used than would be required without the embodiments described herein. Further, tape on an electrode is desirable because it enables the illustrative glucose sensing patch to be hermetically sealed, which may not be possible with another mechanical solution. For example, both a switch or removable tape that breaks the connection to a battery require moving components that may prevent the device from being sealed, or may make it more difficult to hermetically seal the device.

Another illustrative embodiment according to the present disclosure may comprise a device for delivery of therapeutics, e.g., a wearable device with electronics for automatically delivering controlled amounts of a therapeutic, for example wearable pumps for insulin delivery. Another embodiment may be a hand-held drug delivery device with electronics for capturing and tracking drug delivery parameters such as the time that a drug was delivered or the amount of dose selected or delivered. Like a wearable sensor, such a device includes powered electronics and may have a long shelf-life prior to use. An illustrative device for delivering therapeutics may comprise an electrode covered by a passive material (e.g., a mylar tape). When the passive material is removed a separation charge or induced charge generates a voltage across the electrode. This voltage is output to an amplifier circuit, e.g., a single transistor amplifier (e.g., an npn transistor configured as a common emitter amplifier). The amplifier circuit receives the voltage from the electrode, amplifies this voltage, and outputs the amplified voltage to an electronic switch (e.g., a transistor (e.g., a BJT or MOSFET), a relay, an electronically controlled switch, or other switching circuit) to control the flow of current from a power supply (e.g., a battery) to the active components (e.g., processor, memory, sensors, network interfaces, etc.) of the device. Alternatively, in some embodiments the output of the amplifier may be used to wake a processor from a deep-sleep state, such as by disabling a RESET line on the processor or activating a clock. Such an embodiment enables longer life for the device because active components either draw no power or substantially less power prior to removal of the passive material.

In yet another embodiment, a system according to the present disclosure may comprise a smart pill bottle comprising sensor electronics to sense changes in electrical, optical, acoustic or magnetic properties that occur as the lid is rotated with respect to the bottle or as the pill cap is removed from the bottle. This information may be used to measure a user's adherence to a treatment regimen and/or to prevent unauthorized access to substances stored in the pill bottle. As described above, the active components may be in a deep sleep state or unpowered until a passive material is removed from an electrode on the exterior of the device, thus preventing the battery that powers these active components from being degraded during shipment and storage prior to use.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

Illustrative Systems for Peel-Off Detection for Low-Power Electronics

Figure 1A:
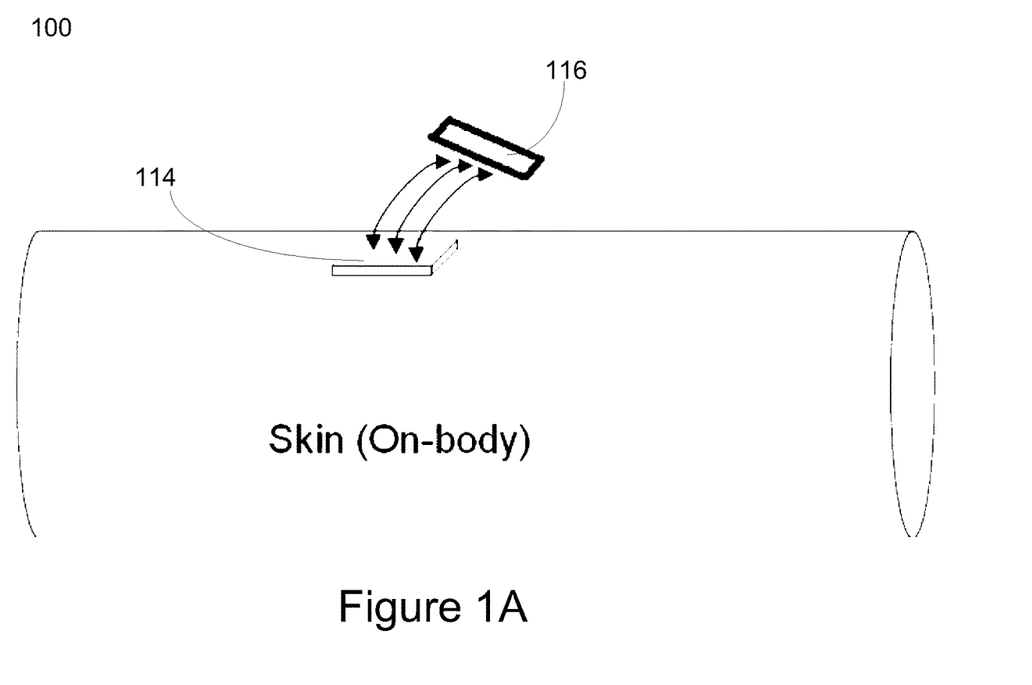
FIG. 1A shows an illustrative system for peel-off detection for low-power electronics according to one embodiment of the present disclosure.

FIG. 1A shows an illustrative system 100 for peel-off detection for low-power electronics according to one embodiment of the present disclosure. As shown in FIG. 1A, the system 100 is an electronic device 114 mounted on a wearer's skin (e.g., at a location on which a sensor of electronic device 114 will be used to take measurements). System 100 further shows a passive material 116 that has been removed from an electrode on electronic device 114 to activate the electronic device 114 as is described in the following paragraphs. In some embodiments, this passive material 116 may comprise a carrier sheet that the device is removed from to expose an adhesive surface of the device that is then affixed to the user's skin.

Figure 1B:
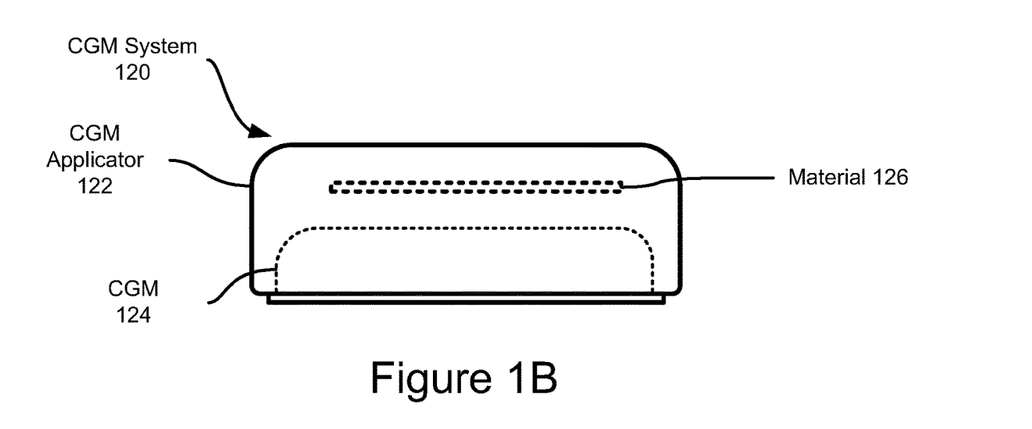
FIG. 1B shows another illustrative system for peel-off detection for low-power electronics according to one embodiment of the present disclosure.

Turning now to FIG. 1B, which shows another embodiment of a system according to the present disclosure. As shown in FIG. 1B, Continuous Glucose Monitor (CGM) system 120 includes a material 126, CGM applicator 122, and the CGM 124. In order to activate the CGM 124 the user removes material 126. This sends a charge to an amplifier which applies power to active components in the CGM 124, e.g., by closing a switch or waking a processor from a deep sleep state.

Figures 1C, 1D:
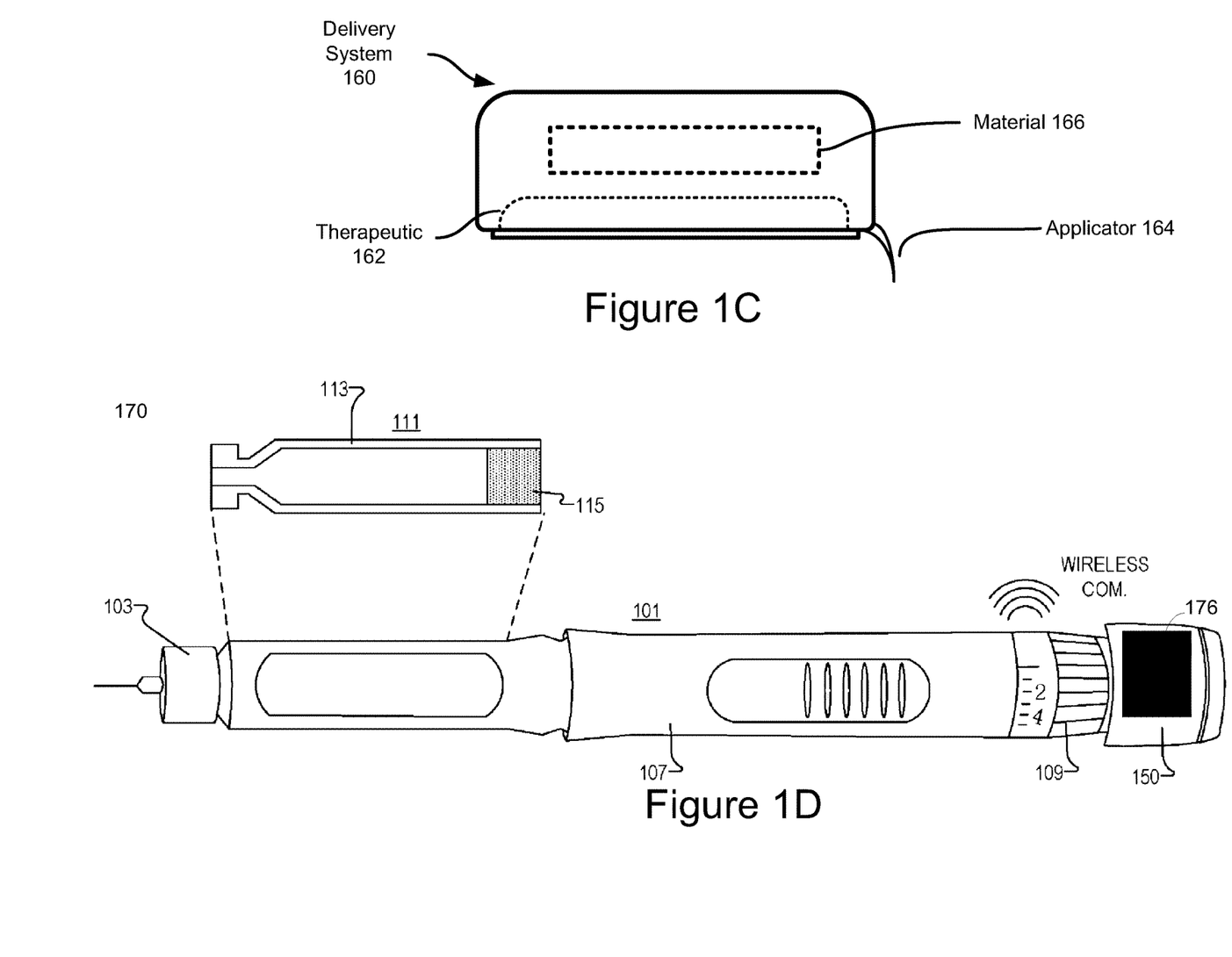
FIG. 1C shows another illustrative system for peel-off detection for low-power electronics according to one embodiment of the present disclosure.
FIG. 1D shows another illustrative system for peel-off detection for low-power electronics according to one embodiment of the present disclosure.

Turning now to FIG. 1C, which shows another illustrative system for peel-off detection for low-power electronics according to one embodiment of the present disclosure. FIG. 1C shows a delivery system 160 including a drug cartridge 162, containing an amount of a therapeutic, an applicator 164 (e.g., a needle or cannula), and material 166. The delivery system 160 is configured to deliver the therapeutic (e.g., insulin, or some other drug or therapeutic) to a wearer via applicator 164 (e.g., a needle). The delivery system 160 may comprise electronics that deliver the therapeutic 162 at programmed times and/or quantities. In order to activate the delivery system 160, the user removes material 166. This sends a charge to an amplifier which applies power to active components in the delivery system 160, e.g., by closing a switch or waking a processor from a deep sleep state.

Turning now to FIG. 1D, which shows another illustrative system for peel-off detection for low-power electronics according to one embodiment of the present disclosure. FIG. 1D shows an injection pen system 170 includes injection pen 101 comprising a drug cartridge 111, which may be in communication with a remote device, e.g., a smartphone, via wireless communication (e.g., Wi-Fi, Bluetooth, BLE, or cellular).

In the embodiment shown in FIG. 1D, drug cartridge 111 includes cartridge body 113, and plunger head 115. In the depicted embodiment, plunger head 115 starts near the rear of drug cartridge 111 and is pushed forward in drug cartridge 111 (with a dosage injection mechanism disposed in injection pen 101). This forces medication/fluid out of the narrow end of drug cartridge 111 when a user chooses to dispense a fluid.

Injection pen 101 is a hand-held device and includes needle 103, body/housing 107 (including a dosage injection mechanism to push in plunger head 115 and extract fluid from drug cartridge 111), and drug delivery control wheel 109 (twist wheel 109 to 'click' select the dosage), and pen button 150 (push button 109 to dispense the selected quantity of the fluid from cartridge 111). Housing 107 is configured to accept cartridge 111, which may be disposed in an insert which screws/snaps onto the bulk of housing 107. Injection pen 101 includes a dosage injection mechanism positioned in the housing 107 to produce a rotational motion and force the fluid out of the cartridge when the drug injection pen 101 dispenses the fluid. A dosage measurement system is also disposed in the pen (e.g., in button 150, stopper 115 or elsewhere in pen body 107) to receive a rotational motion from the dosage injection mechanism. The dosage measurement system may measure a strain induced in a portion of the dosage measurement system by the rotational motion, and the dosage measurement system outputs a signal indicative of the strain when the drug injection pen 101 dispenses the fluid.

A controller is also disposed in drug injection pen 101, and is coupled to the dosage measurement system. This controller is configured to track data associated with the dispensation of the fluid. For example, the controller may track the time, quantity, and frequency that a fluid is dispensed. This information may be stored to measure a user's adherence to a prescribed treatment regimen. Power to active components, such as the controller, is controlled to prevent consumption of power during shipping and storage, thus increasing overall battery life. To activate the injection pen system 170, the user removes material 176. This sends a charge to an amplifier which applies power to active components in the injection pen system, e.g., by closing a switch or waking a processor from a deep sleep state.

Figure 2:
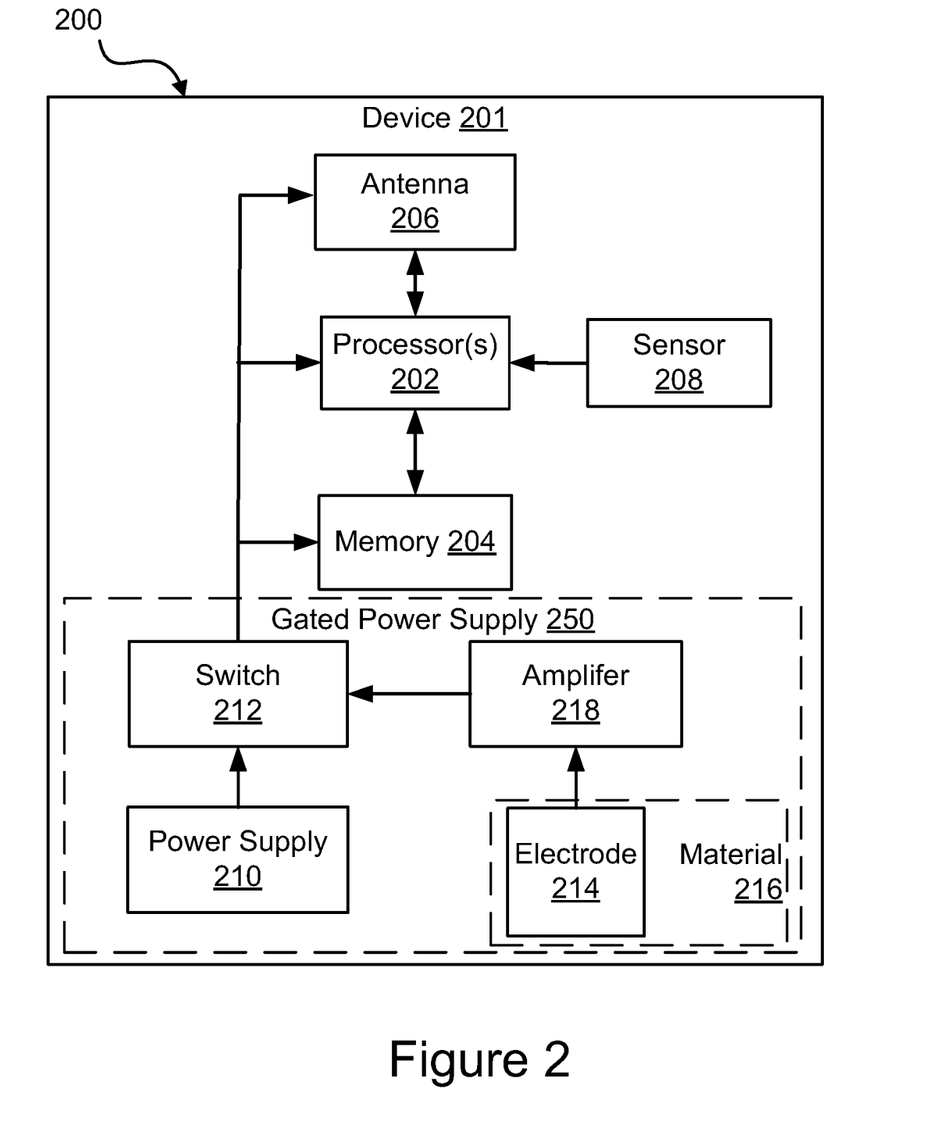
FIG. 2 shows another illustrative system for peel-off detection for low-power electronics according to one embodiment of the present disclosure.

Turning now to FIG. 2, which shows an illustrative system 200 for peel-off detection for low-power electronics according to one embodiment. The system 200 includes wearable device 201, which may include a wearable analyte sensor, e.g., a wearable glucose sensor, hydration sensor, oxygen sensor, or other type of sensor, e.g., a temperature sensor, motion sensor, blood pressure sensor, heart rate sensor, metabolic sensor, or any other type of sensor known in the art. In one embodiment, wearable device 201 includes a wearable patch comprising each of the components shown in FIG. 2.

The wearable device 201 includes a plurality of components that may have an active mode, e.g., a mode in which the device must receive power to operate. These active components include, e.g., processor(s) 202, memory 204, antenna 206, and sensor 208. In some embodiments, these components are not all active components, e.g., in some embodiments, sensor 208 and memory 204 may have both active and passive modes. Alternatively, in some embodiments, one or more of these components may include a passive component, e.g., sensor 208 may be a component that does not have an active mode.

Turning to processor 202, processor 202 comprises one or more of a microprocessor, a digital signal processor (DSP), an application-specific integrated circuit (ASIC), field programmable gate arrays (FPGAs), and state machines. Such processors may further include programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Processor 202 is in communication with memory 204. Memory 204 can include any suitable tangible (and non-transitory) computer-readable medium such as RAM, ROM, EEPROM, or the like, and may embody program components that configure operation of the processor 202 and/or other components of device 201. Memory 204 may further have storage for processor 202 to store data, e.g., data received from a network interface or sensor 208. Memory 204 may be a static memory that can store data while in an unpowered state.

Antenna 206 represents one or more of any components that facilitate a network connection. Examples include, but are not limited to, wired interfaces such as Ethernet, USB, IEEE 1394, and/or wireless interfaces such as IEEE 802.11, Bluetooth, or radio interfaces for accessing cellular telephone networks (e.g., transceiver/antenna for accessing a CDMA, GSM, UMTS, or other mobile communications network(s)). Thus, antenna 206 enables processor 202 to transmit or receive data from a remote device.

Sensor 208 comprises a sensor that measures information about a user, e.g., an analyte sensor, e.g., a wearable glucose sensor, hydration sensor, oxygen sensor, or other type of sensor, e.g., a temperature sensor, motion sensor, blood pressure sensor, heart rate sensor, metabolic sensor, or any other type of sensor known in the art. In some embodiments, sensor 208 may be an active sensor, a passive sensor, or a sensor with both active and passive modes.

As shown in FIG. 2, wearable device 201 further includes a gated power supply 250. The gated power supply 250 includes a power supply 210, a switch 212, an electrode 214, material 216, and amplifier 218.

Power supply 210 is a source of power, e.g., an onboard power source such as a battery, e.g., a rechargeable or non-rechargeable battery, for example, an alkaline battery, aluminum-air battery, aluminum-ion battery, dry cell, lithium battery, magnesium battery, mercury battery, nickel oxyhydroxide battery, lead-acid battery, lithium air battery, lithium ion battery, magnesium ion battery, nickel cadmium battery, sodium ion battery, or any other type of battery known in the art.

Switch 212 is a switch that interrupts the flow of current from power supply 212 to one or more of the active components of wearable device 201. For example, in some embodiments, switch 212 may be a transistor (e.g., a BJT or MOSFET), a relay, an electronically controlled switch, an op-amp circuit, or other switching circuit, e.g., a solid-state or non-solid state circuit that interrupts the flow of current from a power source to a load. Further, after switch 212 is closed it may automatically reopen after a predetermined period of time, e.g., one week or two weeks, or it may stay permanently closed. Further, in some embodiments, switch 212 may be controlled by processor(s) 202 to be opened after the predetermined period of time, thus cutting the flow of current from power supply 210 to the active components.

Turning now to electrode 214, which is a conductive electrical material. In some embodiments, electrode 214 may be a conductor (e.g., copper, aluminum, silver etc.) etched on the inside or outside of a housing associated with device 201. For example, in some embodiments, the electrode 214 may include a copper pattern from a printed circuit board (PCB). The electrode 214 is covered in whole or in part by material 216, which may be a passive material such as tape or mylar. In some embodiments mylar may provide electrostatic shielding, such that there is no false triggering of a charge onto electrode 214 until the mylar is removed. Removing material 216 generates a charge on electrode 214. In some embodiments, electrode 214 may have a rectangular shape that is approximately 4×9 mm. In some embodiments, electrode 214 may be positioned on the interior of a housing of device 201. In such an embodiment, the material 216 may be placed on the exterior of the housing at a location above the location on which the electrode is positioned.

Electrode 214 is further coupled to amplifier 218. When a charge is generated across electrode 214, amplifier 218 amplifies that charge into a control signal that changes the state of switch 212. In some embodiments, amplifier 218 may be a simple amplifier circuit, e.g., an NPN transistor amplifier with minimal components (e.g., a transistor, resistor, and capacitor). In other embodiments, amplifier 218 may be an op-amp circuit or a transistor circuit (e.g., BJT, FET, MOSFET, or HBT circuit) that amplifies an input signal.

In some embodiments material 216 may be tape that prevents a housing of an electronic device from being opened. In such an embodiment, the memory 204 may store data associated with when material 216 was removed. This information may be used to determine if a user has voided the warranty on an electronic device, e.g., by removing the tape to open the case of the device.

In some embodiments, device 201 may have a plastic case that is hermetically sealed. In some embodiments, device 201 may be an electronic device that is manufactured and shipped with switch 212 open, such that very little if any power is consumed until a user receives the electronic device and removes material 216, thus closing switch 212.

Figure 3:
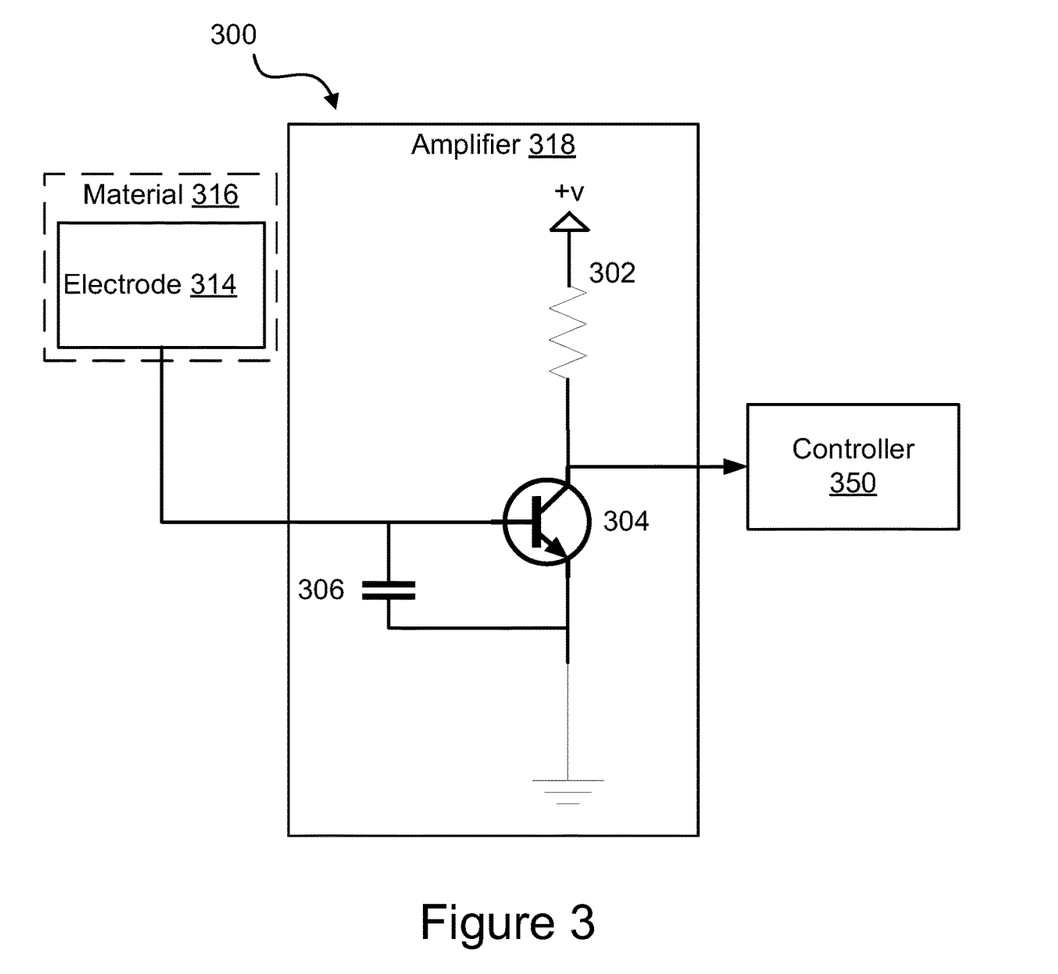
FIG. 3 shows another illustrative system for peel-off detection for low-power electronics according to one embodiment of the present disclosure.

Turning now to FIG. 3, FIG. 3 shows another illustrative system 300 for peel-off detection for low-power electronics according to one embodiment of the present disclosure. As shown in FIG. 3, the system 300 includes an electrode 314 covered by material 316 (which are similar to electrode 314 and material 316 described with regard to FIG. 1A), amplifier 318, and controller 315.

In the embodiment shown in FIG. 3, when a user removes material 316 from electrode 314, a charge is generated and transferred to the electrode 314. This charge is then amplified by amplifier 318. As shown in FIG. 3, the amplifier 318 is a single transistor amplifier circuit. The transistor 304 may comprise a 2N3904 NPN Transistor. The collector may include a 10 MΩ resistor 302 coupled to a voltage (e.g., a voltage provided by power supply 210 discussed above with regard to FIG. 2). The transistor 204 is DC coupled by capacitor 206, which may be a 220 picofarad capacitor.

In the embodiment shown in FIG. 3, the amplifier 318 may amplify the input signal generated when the material 316 is removed from electrode 314). This amplified signal is output by amplifier 318 as a control signal to controller 350. Controller 350 may comprise an electronic switch (e.g., switch 212 described above with regard to FIG. 2). In such an embodiment, the control signal closes the electronic switch and thus provide power to active components (e.g., a processor, a memory, a sensor, etc.). Further, in some embodiments, controller 350 may include a processor. In such an embodiment, the processor may be in a deep-sleep state be woken out of the deep-sleep state by the control signal from amplifier 318.

Figure 4:
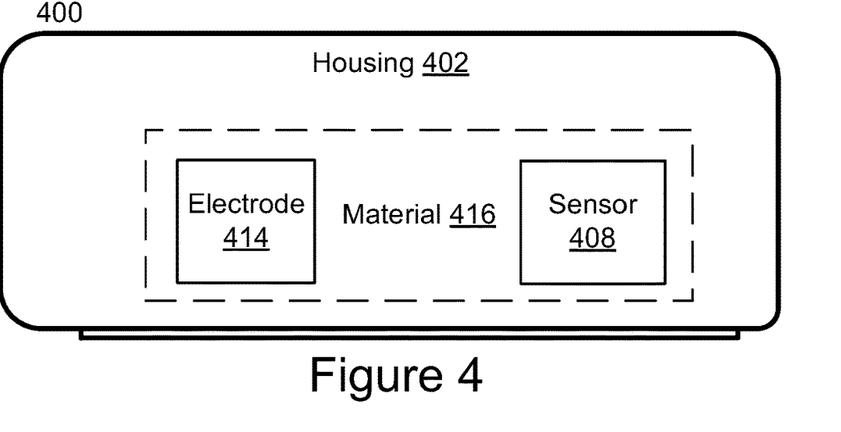
FIG. 4 shows another illustrative system for peel-off detection for low-power electronics according to one embodiment of the present disclosure.

Turning now to FIG. 4, FIG. 4 shows another illustrative system 400 for peel-off detection for low-power electronics according to one embodiment of the present disclosure. As shown in FIG. 4, the system 400 includes housing 402 electrode 414, material 416, and sensor 408. Housing 402 is a housing for an electronic device, e.g., a hermetically sealed housing for a CGM, as described above. The electrode 414 and material 416 are similar to electrode 114 and material 116 described above. As is shown in FIG. 4, the material 416 is positioned such that it must be removed prior to using an associated electronic device. In the embodiment shown in FIG. 4, the material 416 covers part of a sensor 408, e.g., a probe, port, electrode, or sensor wire associated with sensor 408. For example the sensor 408 may be an electrode for an electrocardiogram ("ECG") sensor. Thus, to place the sensor in position the user must remove the material 416 and thereby activate the associated electronic device, as described above.

Figure 5:
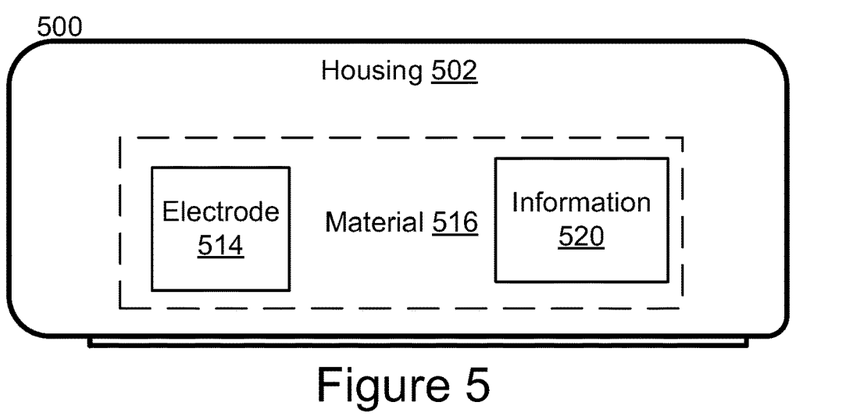
FIG. 5 shows another illustrative system for peel-off detection for low-power electronics according to one embodiment of the present disclosure.

Turning now to FIG. 5, FIG. 5 shows another illustrative system 500 for peel-off detection for low-power electronics according to one embodiment of the present disclosure. As shown in FIG. 5, the system 500 includes housing 502 electrode 514, material 516, and information 520. Housing 502 is a housing for an electronic device, e.g., a hermetically sealed housing for a CGM, as described above. The electrode 514 and material 516 are similar to electrode 114 and material 116 described above. As is shown in FIG. 5, the material 516 is positioned such that it must be removed prior to using an associated electronic device. In the embodiment shown in FIG. 5, the material 516 covers information 520. Information 520 may be information needed to activate an associated device, e.g., instructions, login information, passkey information, etc. In other embodiments, the information 520 is printed on the underside of material 516. Thus, in order to use an associated electronic device the user must remove the material 516 and thereby activate the associated electronic device, as described above.

Figure 6:
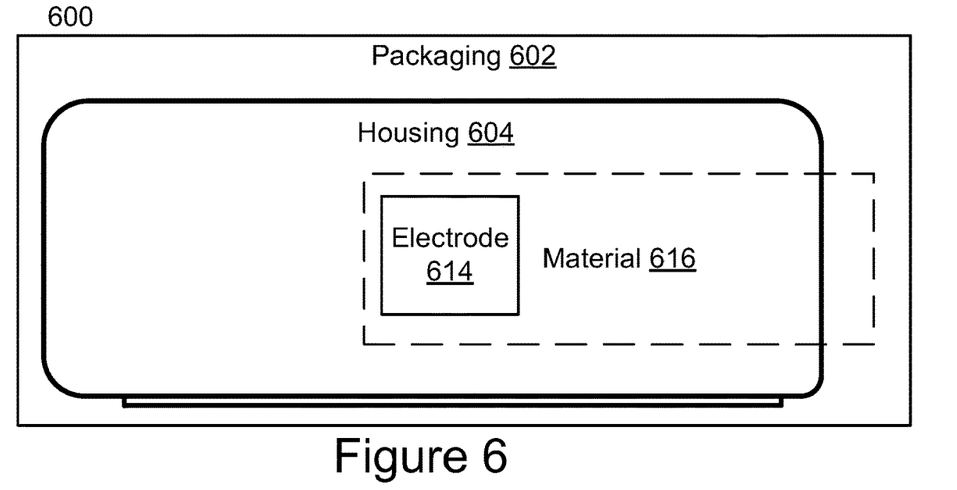
FIG. 6 shows another illustrative system for peel-off detection for low-power electronics according to one embodiment of the present disclosure.

Turning now to FIG. 6, FIG. 6 shows another illustrative system 600 for peel-off detection for low-power electronics according to one embodiment of the present disclosure. As shown in FIG. 6, the system 600 includes housing 604 packaging 602, electrode 614, and material 616. Housing 604 is a housing for an electronic device, e.g., a hermetically sealed housing for a CGM, as described above. The electrode 614 and material 616 are similar to electrode 114 and material 116 described above. As is shown in FIG. 6, the material 616 is positioned such that it must be removed prior to using an associated electronic device. In the embodiment shown in FIG. 6, the material 616 couples housing 604 to packaging 602. Thus, removing housing 604 from packaging 602 requires also removing material 616 from electrode 614 and thereby activate the associated electronic device, as described above.

Illustrative Methods for Peel-Off Detection for Low-Power Electronics

Figure 7:
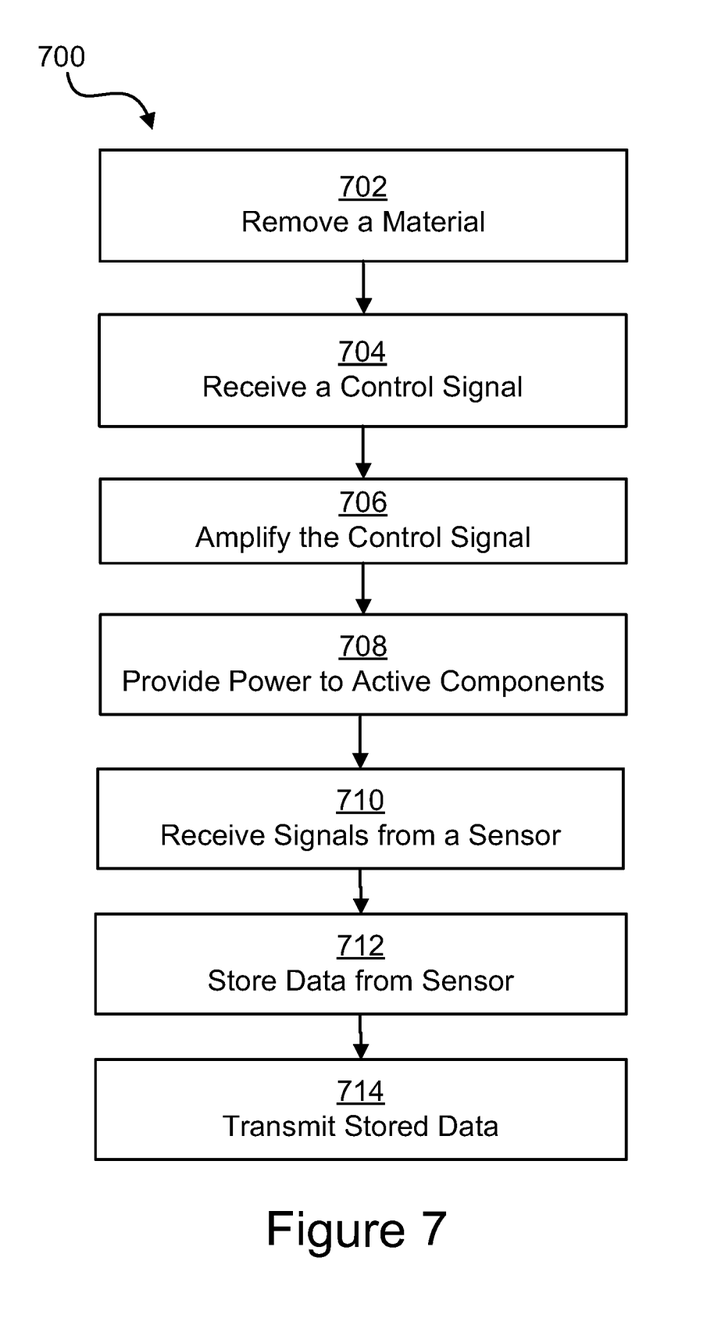
FIG. 7 shows a flow chart of an illustrative method for peel-off detection for low-power electronics according to one embodiment of the present disclosure.

FIG. 7 is a flow chart for a method 700 of peel-off detection for low-power electronics. Alternatively, in some embodiments, one or more of the steps shown in FIG. 7 may be skipped, or additional steps not shown in FIG. 7 may be performed. The steps below are described with reference to components described above with regard to system 200 shown in FIG. 2.

The method 700 begins at step 702, when a material 216 is moved from an electrode 214. Prior to removal of the material 216, the electrode 214 is covered in whole or in part by material 216, which may be a passive material such as tape or mylar. Removing material 216 generates a charge on electrode 214. In some embodiments, the material 216 may further cover part of sensor 208 (e.g., a sensor wire, port, or probe), thus the material 216 must be removed to use the sensor. In other embodiments, the material 216 may cover information (e.g., instructions, login information, passkey information, etc.). Further, in some embodiments, this information may be printed on the underside of material 216. In either case, the user must remove the material to read the information. In still other embodiments, the material 216 may couple the device 201 to packaging (e.g., for shipping). In such an embodiment, the user must remove the material from the electrode 214 to remove the device 201 from its packaging.

The at step 704 amplifier 218 receives a control signal from electrode 214. As described above, removing a material 216 from electrode 214 generates a voltage on electrode 214.

Next at step 706 the amplifier 118 amplifies the control signal. Amplifier 218 is an amplifier circuit that amplifies the voltage on the electrode 214 and apply that amplified voltage as a control signal to switch 212.

Then at step 708 the switch 212 applies power to one or more active components based on the control signal. In one embodiment, the control signal directly triggers the switch 212. In such an embodiment, switch 212 is electrically coupled to amplifier 218 in a configuration such that current from amplifier 218 closes switch 212 and thus provides current to one or more active components on wearable device 201, e.g., processor 202, memory 204, and sensor 208. In some embodiments, the control signal may indirectly control switch 212, for example, by triggering analog or digital circuitry to apply current to switch 212. Further, in some embodiments, switch 212 may be reopened, for example, automatically after a predetermined period of time, or after receipt of a control signal from processor 202.

Then at step 710 processor 202 receives signals from sensor 208. The sensor 208 measures information about a user, e.g., sensor 208 may be an analyte sensor, e.g., a wearable glucose sensor, hydration sensor, oxygen sensor, or other type of sensor, e.g., a temperature sensor, motion sensor, blood pressure sensor, heart rate sensor, metabolic sensor, or any other type of sensor known in the art. In some embodiments, sensor 208 may be an active sensor, a passive sensor, or a sensor with both active and passive modes.

Next, at step 712 the processor 202 stores data received from the sensor 208 in memory 204. Memory 204 may be a static memory, e.g., flash or EEPROM, to store the sensor data received from processor 202 after switch 212 is reopened and power is no longer provided to the active components in wearable device 201.

Then at step 714 the processor transmits the stored data to a remote device. In such an embodiment, the processor 202 may enter a transmit mode, in which the processor 202 transmits the data stored in memory 204 using antenna 206.

The solution described above enables the illustrative glucose sensing patch to have a longer battery life because active components in the glucose sensing patch (e.g., the processor, memory, etc.) do not draw power from the battery until activated by removing the tape. Thus, there is not energy consumed during manufacture, shipping, and storage. This may enable a relatively smaller, lighter, and cheaper battery to be used than would be required without embodiments described herein. Further, tape on an electrode is preferable because it enables the illustrative glucose sensing patch to be hermetically sealed, which is not possible with another mechanical solution. For example, both a switch or removable tape that breaks the connection to a battery require moving components that prevent the device from being sealed.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process that is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered. Accordingly, the above description does not bound the scope of the claims.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

Embodiments in accordance with aspects of the present subject matter can be implemented in digital electronic circuitry, in computer hardware, firmware, software, or in combinations of the preceding. In one embodiment, a computer may comprise a processor or processors. The processor comprises or has access to a computer-readable medium, such as a random access memory (RAM) coupled to the processor. The processor executes computer-executable program instructions stored in memory, such as executing one or more computer programs including a sensor sampling routine, selection routines, and other routines to perform the methods described above.

Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example tangible computer-readable media, that may store instructions that, when executed by the processor, can cause the processor to perform the steps described herein as carried out, or assisted, by a processor. Embodiments of computer-readable media may comprise, but are not limited to, all electronic, optical, magnetic, or other storage devices capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. Also, various other devices may include computer-readable media, such as a router, private or public network, or other transmission device. The processor, and the processing, described may be in one or more structures, and may be dispersed through one or more structures. The processor may comprise code for carrying out one or more of the methods (or parts of methods) described herein.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

What is claimed:

1. A device comprising:
   a housing;
   sensor electronics disposed within the housing;
   only one electrode positioned to receive an induced charge generated by removal of a material from the electrode and output a control signal, the induced charge being characterized by a voltage across the electrode;
   an electronic switch configured to control an electrical connection between a power supply and the sensor electronics; and
   an amplifier electrically coupled to the electrode and configured to receive the control signal from the electrode and output an amplified signal to change a state of the electronic switch based on the control signal.

2. The device of claim 1, further comprising a non-transitory memory configured to store data received from the sensor electronics.

3. The device of claim 2, wherein the non-transitory memory is configured to record that the material was removed.

4. The device of claim 2, wherein the electronic switch is further coupled between the power supply and a processor; and wherein the processor is configured to receive sensor data from the sensor electronics when the electronic switch is closed.

5. The device of claim 4, further comprising a network interface configured to transmit the sensor data stored in the non-transitory memory.

6. The device of claim 5, wherein the housing is hermetically sealed.

7. The device of claim 1, wherein the electronic switch comprises one or more of:
   a transistor, a relay, or an electronically controlled switch.

8. The device of claim 1, wherein, prior to removal, the material covers one or more of: part of a sensor or activation information positioned on the housing.

9. The device of claim 1, wherein the material comprises mylar.

10. An electronic device comprising:
    only one electrode configured to output a control signal based upon an induced charge generated by removal of a material on the electrode, the induced charge being characterized by a voltage across the electrode;
    an electronic switch configured to control an electrical connection between a power supply and one or more active components; and
    an amplifier configured to receive the control signal from the electrode and output a signal to change a state of the electronic switch based on the control signal.

11. The electronic device of claim 10, wherein the electronic switch, the amplifier, and the one or more active components are all positioned within a hermetically sealed housing.

12. The electronic device of claim 10, wherein the one or more active components comprise a memory configured to record that the material was removed.

13. The electronic device of claim 10, wherein the electronic switch comprises one or more of: a transistor, a relay, or an electronically controlled switch.

14. The electronic device of claim 10, wherein prior to removal the material covers one or more of: part of a sensor or activation information positioned on a hermetically sealed housing.

15. The electronic device of claim 10, wherein the material comprises mylar.

16. A method for activating an electronic device comprising:

receiving, by an electrode of the electronic device, an induced charge generated by removal of a material from a housing of the electronic device, the induced charge being characterized by a voltage across the electrode and wherein the electronic device comprises only one electrode;

amplifying, by an amplifier, the induced charge; and closing a switch based on the amplified induced charge to provide power to one or more active components.

17. The method of claim 16, wherein the amplifier and the one or more active components are all positioned within a hermetically sealed housing.

18. The method of claim 16, wherein the one or more active components comprise a memory configured to record that the material was removed.

19. The method of claim 16, wherein prior to removal the material covers one or more of: part of a sensor or activation information positioned on the housing.

20. The method of claim 16, wherein the material comprises mylar.

* * * * *